United States Patent [19]

Dickhudt et al.

[11] 4,257,429
[45] Mar. 24, 1981

[54] STYLET RETAINER AND EXTENSION

[75] Inventors: Eugene A. Dickhudt, New Brighton; Duane J. Zytkovicz, Minneapolis, both of Minn.

[73] Assignee: Medtronic, Inc., Minneapolis, Minn.

[21] Appl. No.: 10,390

[22] Filed: Feb. 7, 1979

[51] Int. Cl.³ .............................................. A61N 1/04
[52] U.S. Cl. .................................... 128/786; 128/348; 128/DIG. 9
[58] Field of Search .................................. 128/784–786, 128/642, 772, 214.4, 348, DIG. 9, 303 R, 419 P

[56] References Cited

U.S. PATENT DOCUMENTS

| 3,416,533 | 12/1968 | Fisher et al. | 128/786 |
| 3,503,385 | 3/1970 | Stevens | 128/DIG. 9 |
| 3,757,768 | 9/1973 | Kline | 128/DIG. 9 |
| 4,046,151 | 9/1977 | Rose | 128/785 |
| 4,103,690 | 8/1978 | Harris | 128/786 |
| 4,146,036 | 3/1979 | Dutcher et al. | 128/785 |

Primary Examiner—Lee S. Cohen

Attorney, Agent, or Firm—Schroeder, Siegrfied, Ryan, Vidas, Steffey & Arrett

[57] ABSTRACT

A medical electrode placement system including a stylet insertable within an electrode carrying lead to provide stability to the lead during electrode placement within the body. The stylet includes a knob secured to one end thereof and a lead engagement device mechanically connected to the knob for imparting movement to a lead in accordance with manipulation of the knob. In a preferred embodiment, the lead engagement device is spaced from the knob to accommodate differences in length from lead to lead and may take the form of a clamp. The lead engagement device may be formed of a body member having a lead accepting groove therein, the groove being configured to compress a lead of desired cross section when placed within the groove. Finger(s) may be provided to project into the lead accepting groove to further enhance the engagement of the lead. In some instances, x-rays may be employed to provide a view of the lead placement. In such instances, the knob may be provided with an extension to remove the hand of the physician from the x-ray or fluoroscopy field.

10 Claims, 4 Drawing Figures

STYLET RETAINER AND EXTENSION

DESCRIPTION

Background of Prior Art

Electrical stimulation of the body is an increasingly important medical procedure. For example, the circumstances in which the well known cardiac pacemaker is employed have expanded considerably. Other electrical stimulators are similarly gaining in acceptance.

A complicating factor encountered in many stimulating contexts is the need to precisely position the electrode and maintain that position. For example, nerve stimulation is often selective requiring precision in the placement of the electrode. A later movement of the electrode is destructive to the effectiveness of the stimulation and may render the stimulation totally ineffective.

One tactic employed to reduce the incidence of electrode movement is to provide a high flexibility throughout the length of the electrode carrying lead. In this manner, the lead will more easily deflect, elongate and/or compress in response to a force applied to the lead body with less transmittal of that force to the electrode. Thus, a high flexibility lead contributes to stability of the electrode position. However, such flexibility hinders the placement of the electrode in that the lead will bend under the influence of a force whose intended result is advancement of the lead along its desired path.

To overcome the difficulties that arise from the flexibility of the lead during electrode placement, it is known to form the lead conductor as a helical coil and employ a stylet positioned within the coil lumen to provide stability to the lead. Such a system is disclosed in U.S. Pat. application Ser. No. 926,100, filed July 19, 1978 in the name of Alfred A. Iverson for BODY STIMULATION LEAD, which application is co-owned with the present invention and is hereby incorporated by reference. As noted in the incorporated specification, the stylet not only provides stability to the lead but also straightens the lead.

As the electrode is directed towards its intended position, it is not uncommon for it to encounter obstacles. One technique employed by physicians in such situations, is to slightly deflect or bend the tip of the lead such that the lead will deflect around obstructions. Also, the tip of the lead and/or electrode may be made radiopaque such that the movement of the lead and electrode may be viewed by x-ray or fluoroscopy. With such viewing, the deflected tip of the lead may be rotated as obstacles are encountered to insure that the electrode movement is toward the desired location. Within the context of the incorporated specification, such rotation of the electrode is a two-handed operation in that one hand is maintained on the stylet while the other manipulates the lead itself.

BRIEF SUMMARY OF THE INVENTION

The present invention is directed to an electrode placement system of the type having a stylet insertable within an electrode carrying lead to provide stability to the lead during electrode placement within the body. A knob is provided at one end of the stylet and lead engagement means are mechanically connected to the knob for engagement with the lead to impart movement to the lead in accordance with manipulation of the knob. In this manner, a bent or deflected lead and/or electrode tip can be rotated in a single, one-handed operation. Also, the knob may be provided with an extension to position the physician's hand outside an x-ray or fluoroscopy field. In a preferred embodiment, the lead engagement means is spaced from the knob in a direction generally along the stylet and is formed as a clamp. Specifically, the lead engagement means may be formed as a body member having a lead accepting groove, the groove being configured to compress a lead of desired cross-section. Fingers may be provided to project into the lead accepting groove and further enhance the engagement of the lead.

DETAILED DESCRIPTION OF INVENTION

Figure 1:
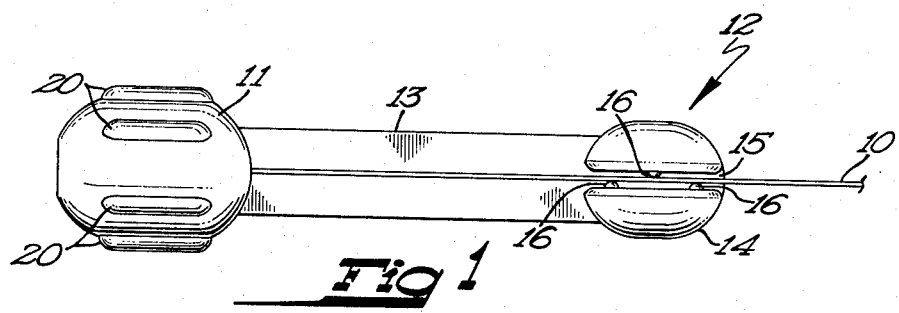
FIG. 1 is a top view of a preferred embodiment of the present invention.

Referring now to FIG. 1, there is shown a top view of the preferred embodiment of the present invention. A stylet 10 of conventional design has one end secured within or to a knob 11. The stylet 10 has a cross-section small enough to fit within a lumen in a lead whose electrode it is desired to position. Typically, the stylet 10 is of sufficient length to extend throughout the length of the lead lumen and engage the electrode it carries.

A lead engagement means indicated generally at 12, is spaced from knob and mechanically secured to the knob 11 by a link 13. The knob 11, engaging means 12 and link 13 may be formed as a unitary structure, as by molding, for example. Any material that may be sterilized and is otherwise suitable for the medical environment may be employed to form components 11–13. The material of the stylet 10 may be that currently in use in the prior art. The stylet 10 may be secured within the knob 11 during the molding process or may be otherwise secured, in known manner.

Engaging means 12 is formed of a body member 14 having a groove 15. The groove is adapted to accept a lead and is preferably configured to compress a lead of desired cross-section when that lead is placed within the groove 15. Fingers 16 may be provided to project into the lead accepting groove 15 to enhance the engagement of a lead within that groove.

Figure 2:
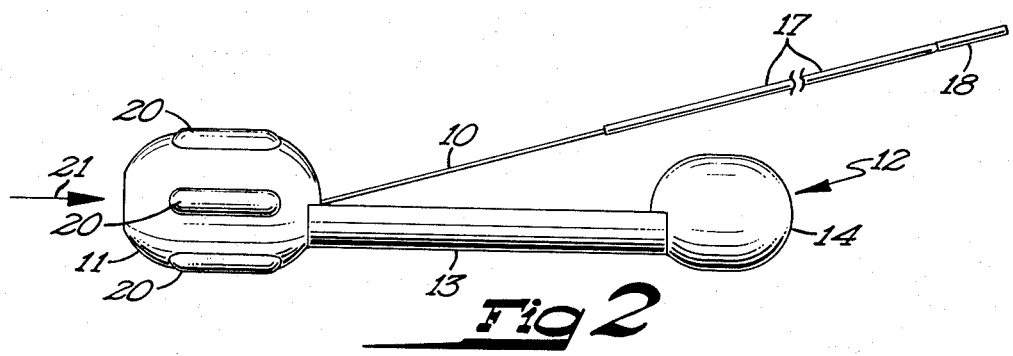
FIG. 2 is a side view of a preferred embodiment of the present invention with the stylet positioned within a lead.

FIG. 2 illustrates a side view of the embodiment of FIG. 1 with the stylet in position in a lumen of a lead whose electrode it is desired to position. The stylet should be of such length that it extends throughout the lead, to provide stability to the entirety of the lead, and contacts an electrode carried by the lead. In FIG. 2, the lead body is indicated at 17 with the electrode being indicated at 18. The lead body 17 should terminate in the space intermediate the knob 11 and body member 14. With the stylet 10 fully inserted within the lumen within lead body 17, the lead body 17 may be forced into the groove 15, preferably to be compressed therein and engaged by the fingers 16 (see FIG. 1) to securely engage the lead body 17. With the lead body 17 within the groove 15 of body member 14, manipulation of the knob 11 will result in the imparting of a corresponding movement to the lead body 17.

Figure 3:
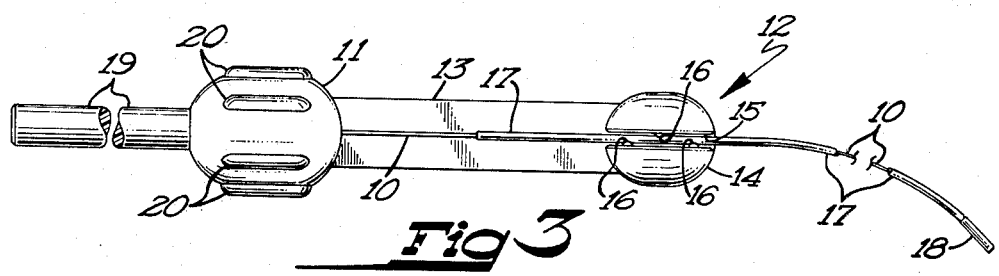
FIG. 3 is a top view of a preferred embodiment of the present invention with the stylet inserted within the lead and with an extension provided to the knob.

FIG. 3 illustrates a top view of the embodiments of FIGS. 1 and 2 with a lead positioned within the groove 15 of body member 14. As noted above, the groove is preferably configured to compress the lead when the lead is positioned within it and the fingers 16 extend into the groove 15 to further enhance the engagement of the lead within the groove. The spacing between the knob 11 and body member 12 allows for variations in a lead length in that the lead may terminate at any point between those elements and still be reliably engaged by the body member 12. As indicated above, it is a common practice to deflect the lead adjacent the tip to facilitate the movement of the electrode and lead past obstacles along its desired path. This is illustrated in FIG. 3. Also, the tip of the electrode 18 and/or the lead body 17 adjacent the tip 18 may be radioopaque to allow a viewing of the passage of the lead and electrode via x-ray or fluoroscopy. In this event, it is desirable to provide an extension for the knob 10 such that the physician's hand is out of the x-ray or fluoroscopy field during positioning of the electrode. Such an extension is indicated at 19 in FIG. 3 which may be a rod inserted within a hole of corresponding size in the end of knob 11. The extension rod 19 may be of the same material as that forming elements 11-13.

Figure 4:
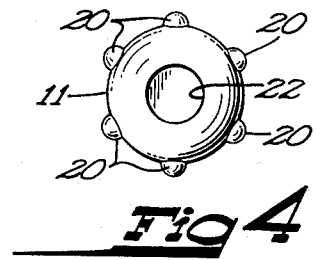
FIG. 4 is an end view of the knob of the embodiments of FIGS. 1–3.

To facilitate manipulation of the knob 11, it is provided with a series of upstanding projections 20 positioned around its periphery. These projections are best illustrated in FIG. 4 which is an end view of knob 11 as viewed in the direction of arrow 21 in FIG. 2. FIG. 4 also illustrates a hole 22 which is adapted to receive and retain the extension 19, by friction, for example. The extension rod 19 may be of any desired length.

Many modifications and variations of the present invention are possible in light of the above teachings. For example, the lead engagement means need not be formed as a clamp as in the illustrated embodiment. In addition, the lead engagement means may be carried more closely to or directly by the knob 11 so long as manipulation of the knob 11 results in the imparting of a corresponding movement to a lead body 17. In this manner, placement of the electrode 18 may be a single-hand operation. It is therefore to be understood that, within the scope of the appended claims, the invention may be practiced otherwise than as specifically described.

We claim:

1. In a medical electrode placement system of the type wherein a stylet is inserted within a flexible body portion of an electrode carrying lead to provide stability to the flexible lead body portion during electrode placement, the improvement which comprises knob means secured to one end of said stylet and lead engagement means mechanically connected to said knob means for engaging said flexible lead body portion to impart movement to the lead in accordance with manipulation of said knob means.

2. The system of claim 1 wherein said lead engagement means is spaced from said knob means generally along said stylet to accommodate different lead body lengths.

3. The system of claim 1 further comprising means for providing a knob means extension.

4. The system of claim 3 wherein said knob means extension means comprises rod means extending from said knob means.

5. The system of claim 1 wherein said lead engagement means comprises clamp means.

6. The system of claim 1 wherein said lead engagement means comprises a body member having groove means for accepting a lead therein.

7. The system of claim 6 wherein said lead accepting groove means comprises means for compressing a lead of desired cross section.

8. The system of claim 7 wherein said lead compressing means further comprises finger means groove projecting into said lead accepting groove means.

9. The system of claim 8 further comprising means for providing a knob means extension.

10. The system of claim 9 wherein said knob means extension means comprises rod means extending from said knob means.

* * * * *